US008152734B2

(12) United States Patent
Noffsinger et al.

(10) Patent No.: US 8,152,734 B2
(45) Date of Patent: Apr. 10, 2012

(54) SYSTEM AND METHOD FOR DIAGNOSIS OF BOVINE DISEASES USING AUSCULTATION ANALYSIS

(75) Inventors: Thomas H. Noffsinger, Benkelman, NE (US); Garrett W. Taylor, Oakley, KS (US); Wade A. Taylor, Oakley, KS (US)

(73) Assignee: Pierson Precision Auscultation, Oakley, KS (US)

( * ) Notice: Subject to any disclaimer, the term of this patent is extended or adjusted under 35 U.S.C. 154(b) by 707 days.

(21) Appl. No.: 12/267,448

(22) Filed: Nov. 7, 2008

(65) Prior Publication Data

US 2009/0137918 A1  May 28, 2009

Related U.S. Application Data

(60) Provisional application No. 60/990,834, filed on Nov. 28, 2007.

(51) Int. Cl.
*A61B 5/08* (2006.01)
(52) U.S. Cl. ............................................ 600/529
(58) Field of Classification Search .................. 600/529
See application file for complete search history.

(56) References Cited

U.S. PATENT DOCUMENTS

| | | | |
|---|---|---|---|
| 4,720,866 A | 1/1988 | Elias et al. | |
| 4,928,705 A | 5/1990 | Sekhar et al. | |
| 5,025,809 A | 6/1991 | Johnson et al. | |
| 5,165,417 A | 11/1992 | Murphy, Jr. | |
| 5,218,969 A | 6/1993 | Bredesen et al. | |
| 5,255,685 A | 10/1993 | Parra | |
| 5,301,679 A | 4/1994 | Taylor | |
| 6,053,872 A | 4/2000 | Mohler | |
| 6,261,238 B1 | 7/2001 | Gavriely | |
| 6,309,352 B1 | 10/2001 | Oraevsky et al. | |
| 6,394,967 B1 | 5/2002 | Murphy, Jr. | |
| 6,396,931 B1 | 5/2002 | Malilay | |
| 6,418,876 B1 | 7/2002 | Hall et al. | |
| 6,443,907 B1 | 9/2002 | Mansy et al. | |
| 6,520,924 B2 | 2/2003 | Lee | |
| 6,706,002 B1 | 3/2004 | Halleck et al. | |
| 6,887,208 B2 | 5/2005 | Kushnir et al. | |
| 6,949,075 B2 | 9/2005 | Hatlesad et al. | |
| 6,953,436 B2 | 10/2005 | Watrous et al. | |
| 6,979,298 B2 | 12/2005 | Vodyanoy et al. | |
| 7,066,894 B2 | 6/2006 | Halleck et al. | |
| 2005/0014999 A1 | 1/2005 | Rahe-Meyer | |
| 2005/0137464 A1 | 6/2005 | Bomba | |
| 2006/0253005 A1 | 11/2006 | Drinan | |
| 2007/0088194 A1* | 4/2007 | Tahar et al. ................ 600/102 |
| 2008/0013747 A1* | 1/2008 | Tran ................................ 381/67 |

FOREIGN PATENT DOCUMENTS

| | | |
|---|---|---|
| AU | 2005/100352 | 6/2005 |
| EP | 0956821 | 11/1999 |

OTHER PUBLICATIONS

Ferrari et al. (Preventative Veterinary Medicine. 2010; 96: 276-280.).*
International Search Report for International (PCT) Patent Application No. PCT/US2009/060080, mailed Dec. 3, 2009.
Written Opinion for International (PCT) Patent Application No. PCT/US2009/060080, mailed Dec. 3, 2009.
"Auscultation", Wikipedia, available at http://en.wikipedia.org/wiki/Auscultation, accessed Nov. 13, 2007, pp. 1-2.
"Fourier Transform", Wikipedia, available at http://en.wikipedia.org/wiki/Fourier_transform, accessed Nov. 9, 2007, pp. 1-14.
"Stethoscope", Wikipedia, available at http://en.wikipedia.org/wiki/Electronic_stethoscope, accessed Nov. 13, 2007, pp. 1-3.
"WAV", Wikipedia, available at http://en.wikipedia.org/wiki/WAV, accessed Nov. 9, 2007, pp. 1-3.
"WAVE File Format", available at http://www.borg.com/~jglatt/tech/wave.htm, accessed Nov. 9, 2007, pp. 1-10.
Car et al., "The Role of leucocytes in the pathogenesis of Fibrin Deposition in Bovine Acute Lung Injury", Am J Path 138 (5):1191-1198, 1991.
Robinson, "Some functional Consequences of species differences in lung anatomy", Advances in Veterinary Science and Comparative Medicine, vol. 26, pp. 1-33.
Thomson, "The pathogenesis and Lesions of Pneumonia in Cattle", Compendium Cont Ed Pract Vet 7(11): s403-S411,1981.
Veit et al., "The Anatomy and Physiology of Bovine Resp System relating to Pulmonary Disease" Cornell Vet 68:555-581 1978.
Weekley et al., "Potential Morphologic and Physiologic factors that predispose the Bovine Lung to Resp Disease", Compendium Contin Education Pract Vet 17(7):974-982,1995. Noffsinger, "Lung Auscultation and Sick Calf Management", date unknown, pp. 1-68.
Robinson et al., "Physiology of the Bovine Lung," Departments of Physiology and Large Animal Clinical Sciences, Michigan State University, pp. 192-222, date unknown.
International Preliminary Report on Patentability for International Patent Application No. PCT/US2009/060080, mailed May 19, 2011 8 pages.

* cited by examiner

*Primary Examiner* — Shanon A Foley
(74) *Attorney, Agent, or Firm* — Sheridan Ross, P.C.

(57) ABSTRACT

A system and method are provided for diagnosis of bovine respiratory diseases using auscultation techniques. Acoustic characteristics of a recorded spectrogram are compared with existing data enabling a diagnosis to be made for a diseased animal. Lung sounds are obtained by use of an electronic stethoscope, and the sounds are stored as digital data. Signal conditioning is used to place the data in a desired format and to remove undesirable noise associated with the recorded sounds. An algorithm is applied to data, and lung scores are calculated. The lung scores are then categorized into various levels of perceived pathology based upon baseline data that categorizes the lung scores. From the lung scores, a caregiver can associate a diagnosis, prognosis, and a recommended treatment. Analysis software generates the lung scores from the recorded sounds, and may also provide a visual display of presumptive diagnoses as well as recommended treatments.

19 Claims, 8 Drawing Sheets

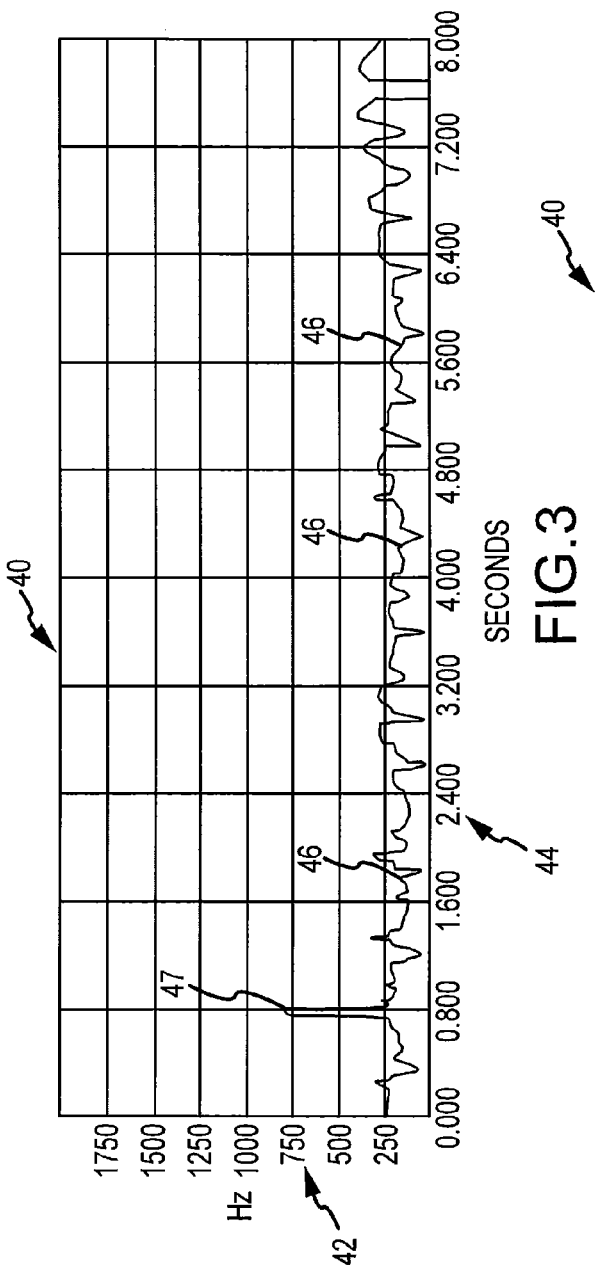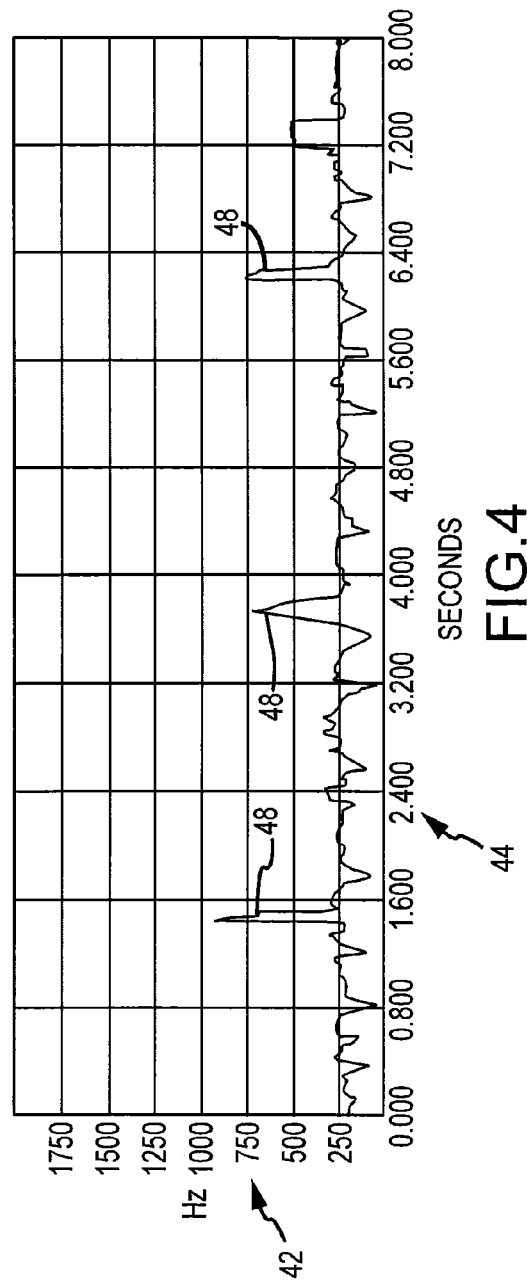

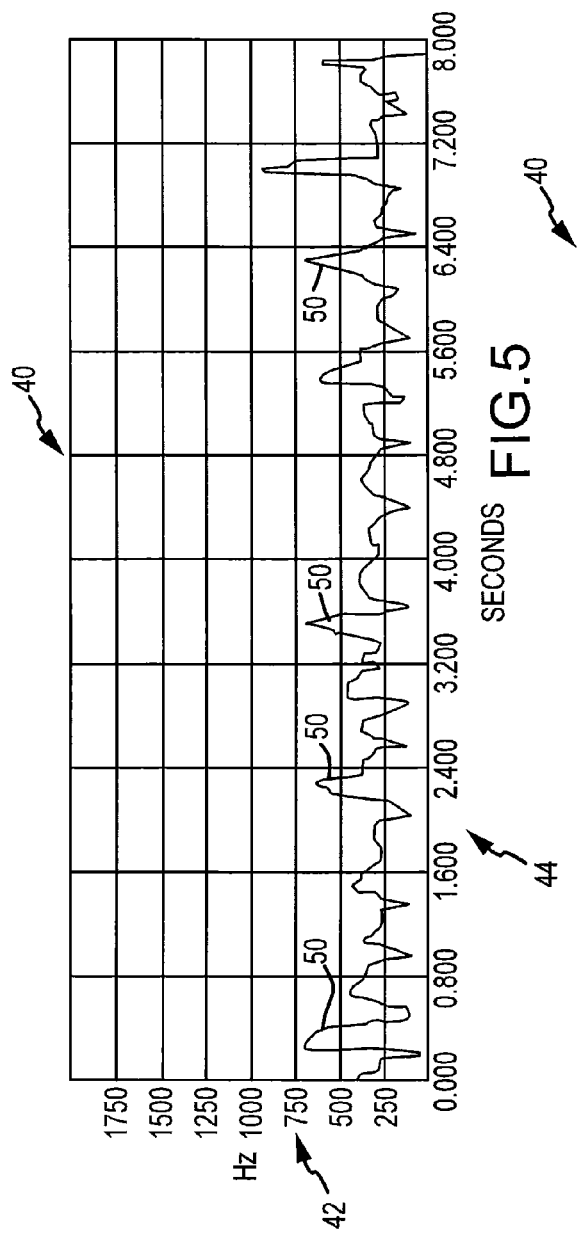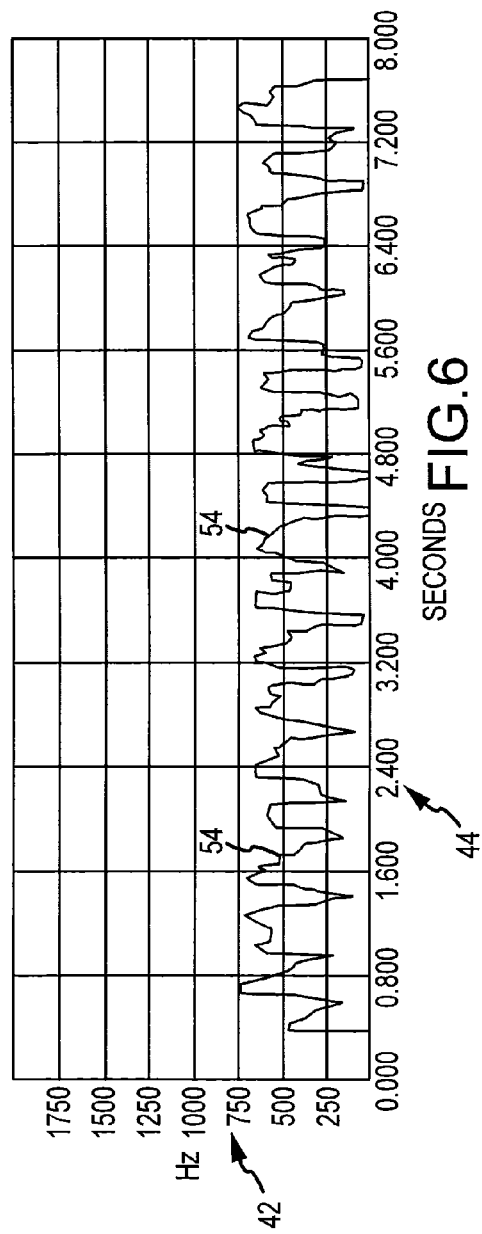

SYSTEM AND METHOD FOR DIAGNOSIS OF BOVINE DISEASES USING AUSCULTATION ANALYSIS

CROSS REFERENCE TO RELATED APPLICATION

This application claims priority from U.S. Provisional Patent Applicant No. 60/990,834 filed Nov. 28, 2007, which is incorporated by reference herein in its entirety.

FIELD OF THE INVENTION

The present invention generally relates to non-invasive diagnosis of diseases for animals, and more particularly, to a system and method for diagnosis of bovine respiratory diseases using auscultation techniques. The acoustic characteristics of recorded sounds are placed in a digital data format, and then are manipulated in one or more mathematical operations including an algorithm to generate a numerical lung score. The lung scores are compared to existing data that indicate the level of disease in the observed animal. Diagnosis, prognosis, and treatment recommendations can also be generated based upon the lung scores.

BACKGROUND OF THE INVENTION

Cardiovascular diseases, respiratory diseases, and gastrointestinal diseases have been distinguished according to sounds auscultated from the body of a patient. Based upon measurements taken of the different sounds, medical practitioners have been able to diagnose diseases and proceed with treatments.

In order to make a precise diagnosis of an ailment based upon auscultated sounds, extensive empirical knowledge of various and diverse forms of auscultated sounds is necessary. Until recently, auscultation was more art than science since making a diagnosis was based mainly upon the trained ear of a caregiver and not based upon measured data from recorded sounds.

With the advent of digital/electronic stethoscopes, auscultated sounds can be recorded in digital form, and software programs can then manipulate the data in order to analyze characteristics of the data. From this analysis, more precise diagnoses can be made based upon objective criteria and not just upon the trained ear of the attending caregiver.

It is well known to measure auscultated sounds from humans in order to make diagnoses of perceived ailments. However, auscultation for animals such as cattle is used infrequently. There have been very few efforts made to gather data for auscultated bovine sounds for purposes of making conclusions as to the type of disease that may be occurring in bovine species.

Particularly in a feed yard where it is necessary for cattle to be maintained at an optimum state of health for the necessary weight gain to occur, it is critical that sick cattle be identified early for effective treatment and to contribute to biosecurity. The true state of health for cattle can be difficult to measure using traditional techniques such as observation of symptoms to include temperature, posture and visual signs (e.g. nasal discharge, depression, and abdominal fill.) Case definitions for Bovine Respiratory Disease have traditionally included an objective minimal rectal temperature and a subjective clinical score. Clinical trials indicate that objective lung scores provide stronger correlations than rectal temperatures to ultimate case fatality rates, retreatment rates, and treatment costs. Cattle are visually evaluated when they first arrive at the feed yard, and adrenalin associated with handling can often mask disease symptoms. Stethoscopic evaluation of bovine lung sounds can be used to evaluate the oxygen metabolism potential of cattle during various stages of arrival processing. However, because of the lack of current data in objectively categorizing bovine lung sounds, there is a need for developing an automated system and method that can assist a caregiver in assessing these lung sounds and making timely diagnoses.

Bovine respiratory disease is complex and is particularly difficult to treat and diagnose compared to respiratory diseases in humans. The thick musculature that surrounds the thorax of cattle, the heavy hide and possible layers of fat, and the breadth of the ribs complicates the use of a stethoscope to obtain sounds that can be analyzed for purposes of making a diagnosis.

Because of problems associated with effectively gathering auscultated sounds from cattle, and the general lack of knowledge as to how to analyze these sounds, the cattle industry has been slow in developing automated diagnostic processes that can effectively use auscultated data.

One patent reference that discusses the use of acoustics for detection of respiratory conditions is the U.S. Pat. No. 6,443,907. This reference specifically discloses diagnostic techniques to enable detection of respiratory conditions within a patient's body. Data gathered from auscultation is compared to reference acoustic characteristics and/or predetermined threshold values to determine if an abnormal respiratory condition is present within the patient. The diagnostic technique includes the processing of acoustic data by calculating energy ratios using energy values within high and low frequency bands, signal time delays, and/or dominant frequencies; the calculated values are then compared to predetermined reference thresholds to generate outputs indicative of the respiratory condition within the patient.

The U.S. Pat. No. 6,520,924 discloses an automatic diagnostic apparatus using a digital stethoscope. The diagnosis is determined based upon a comparison of recorded auscultated sounds versus standard data of auscultated sounds for cardiovascular, respiratory, and gastrointestinal diseases. Objective criteria are used to compare the collected auscultated sounds and the standard data to enable a medical practitioner to diagnose a particular disease.

Although auscultation has been well developed for human treatment, there is clearly a need for an automated process and method that can diagnose bovine respiratory diseases.

SUMMARY OF THE INVENTION

In accordance with the present invention, a system and method are provided for diagnosing respiratory diseases of bovine species. Stethoscopic evaluation of bovine lung sounds is used to gather data on the sounds. Collection of lung sounds is preferably obtained by a digital/electronic stethoscope that is capable of expressing sounds in the form of a spectrogram. Collected digital data from the stethoscope is manipulated by computer software that allows real time analysis of the spectrogram and the diagnosis of an ailment based upon numerical lung scores that generally categorize the health of the animal. The lung scores are compared with threshold levels that generally describe the health of the animal and can be further interpreted to correspond to a certain level of disease in the animal. This comparison may also be used to generate one or more recommended treatments. The assigning of numerical lung scores to evaluated cattle is an efficient predictor of respiratory problems.

Through extensive data gathering, it has been found that auscultated sounds from bovine species that fall within particular frequency ranges provide an indication of respiratory disease. Assuming that the stethoscope is placed at the proper location to collect auscultated sounds, collected sounds falling within these frequencies are converted through a series of mathematical operations including one or more algorithms to produce the numerical lung scores. These lung scores then correspond to various levels of respiratory disease and, accordingly, diagnosis, prognosis, and treatment can then be pursued based upon the specific lung scores obtained.

More specifically, it has been determined through testing that auscultated sounds in a range between 500-900 Hz can be used to generate the numerical lung scores and therefore indicate various levels of respiratory disease.

In accordance with the method of the present invention, the auscultated sounds are collected from bovine species by use of a digital stethoscope that is placed approximately three inches above the right elbow of the animal, thereby placing the stethoscope over the right apical lobe. Sounds can also be gathered on the left side approximately three inches above the left elbow, thereby placing the stethoscope over the cardiac lobe. Once the sounds have been gathered and recorded by the digital stethoscope, the data is downloaded to a computing device. The recorded sound is preferably loaded as a .wav file. If another file format is used, in accordance with the present invention, the software is adapted to convert to the .wav format for processing. A .wav file is an industry standard waveform audio format that is used for storing audio on devices such as personal computers. This file is a variant of the RIFF bit-stream format method for storing data in groups, and is presently the main format used on Windows systems for raw audio data. The data recorded from the sound is stored in an array in its raw or basic format. A short-time Fourier transform (STFT) is performed on the raw data with a selected window size of approximately 512 data points and an approximate 50% overlap. The window size refers to the amount of data that each Fourier transform will cover. Each window is overlapped with approximately 50% of the previous window to help improve frequency resolution. Because a Fourier transform functions only with an infinite stationary signal, the dynamic signals recorded have to be separated into many small pieces so that each piece can represent a stationary value at that time. The window size selected has an effect on how accurate of a frequency representation the transform outputs, and a window size of approximately 512 data points has been shown to provide the requisite accuracy for purposes of generating lung scores in accordance with the present invention. For example, sounds sampled at 4000 Hz by a particular type of digital stethoscope could contain 8192 raw data points for every second of recorded sound. The STFT will take the first 512 of these data points and operate on them. The second sweep, because of the overlap, will start at the 256th data point and progress to the 767th data point. This combination of window size and overlap has been shown to provide a good trade off between frequency resolution and time resolution.

Through testing, it has been found that the specific windowing function may include a Hamming function. As understood by those skilled in the art, a Hamming function zeroes the data outside of a specified interval. Windowing functions are used in short time Fourier transforms (STFT) to help combat the problem of spectral leakage. The Hamming function has been shown to help create better frequency resolution, such that the frequencies contained in the recorded sound can be more accurately represented.

The resulting data from each Fourier transform is plotted on a graph to form data points for a spectrogram. In accordance with the present invention, the plotted data creates a spectrogram that is a visual representation of the recorded sounds in the frequency domain where the plotted axes are time and frequency. Amplitudes of frequencies between about 500-900 Hz are the most important in terms of differentiating between varying categories of sounds corresponding to various levels of respiratory disease. The data is then separated into ten primary sets or bands, namely, amplitudes between 500-540 Hz, 540-580 Hz, 580-620 Hz, 620-660 Hz, 660-700 Hz, 700-740 Hz, 740-780 Hz, 780-820 Hz, 820-860 Hz, 860-900 Hz.

Each frequency band is trimmed to remove the first and last portion of the recorded sound. The trimming function can be achieved through the use of a user selection screen in a computer software program that generates a spectrogram of the recorded sound. The user can manually trim the applicable first and last portion of the recorded sound by viewing the recorded sound in the spectrogram and using the prescribed software function to remove the desired portions of the recorded sound. The user also evaluates the recorded sound as a whole in order that only the pertinent sections of each recorded sound are selected for analysis, thereby ensuring that any unnecessary data is not included. For example, with the use of some stethoscopes, when the stethoscope is first placed on an animal, a significant popping sound may be recorded. This popping sound is easily removable by the user deleting or removing the portion of the spectrogram that corresponds to the popping sound in the user selection screen. The resulting frequencies obtained may be referred to as trimmed frequencies. Each of the ten trimmed frequency bands is then fed to a finite impulse response (FIR) filter, such as a 125 tap FIR filter with identical coefficients. For purposes of this calculation, auscultated sounds over a period of three full respirations of the animal are adequate for effective scoring. In order to account for differences in the respiration rates of animals and any noise that may be present, it has been found that recording sounds over an 8 second period of time is adequate. This time frame however can be modified to account for any unusual circumstances at the time of auscultation.

The numerical results of applying each FIR filter is then used to formulate a calculated numerical lung score that is compared to established baseline data for establishing a presumptive diagnosis of disease severity.

The formula or equation for establishing lung scores can therefore be expressed as follows where the X values are the numerical result of applying the FIR filter in the stated frequency range:

$x_1$=result of 500-540 Hz FIR filter; $x_2$=result of 540-580 Hz FIR filter;

$x_3$=result of 580-620 Hz FIR filter; $x_4$=result of 620-660 Hz FIR filter;

$x_5$=result of 660-700 Hz FIR filter; $x_6$=result of 700-740 Hz FIR filter;

$x_6$=result of 700-740 Hz FIR filter; $x_7$=result of 740-780 Hz FIR filter;

$x_8$=result of 780-820 Hz FIR filter; $x_9$=result of 820-860 Hz FIR filter;

$x_{10}$=result of 860-900 Hz FIR filter;

score=$0.205x_1+0.075x_2+0.02x_3+0.2x_4+0.35x_5+0.02x_6+0.02x_7+0.09x_8+0.01x_9+0.01x_{10}$ The coefficients in the lung score equation were determined by gathering data on a large number of sounds, and comparing the sounds to determine if a numerical relationship could be established that correlated the results of applying the FIR filter to sounds in the various frequency ranges with a presumptive diagnosis. The coefficients were established in such a way that the lung scores could be calculated in an increasing order from healthiest (smallest) to sickest (largest), and such that the lung score categories could be easily divided to correspond to various discrete diagnoses. From this exhaustive data gathering and mathematical development exercise, the lung score equation was derived.

Once a calculated lung score is obtained, it is compared to baseline data in the form of threshold values that generally correspond to bovine respiratory conditions. These threshold values have been established as a result of a number of tests in which the threshold values consistently show a direct relationship with the state of health of the animal being evaluated. The threshold values can be expressed in terms of a Scaled Lung Score between 1 and 9. These Scaled Lung Scores may be easier for the caregiver to record and report as opposed to the actual calculated lung scores. As listed below, a bovine respiratory condition is indicated as a function of a range of calculated lung scores and a corresponding Scaled Lung Score. Thus, the range of calculated lung scores as they correspond to respiratory conditions and the Scaled Lung Scores are as follows:
  a. Scaled Lung Score 1 (Low Normal)=calculated lung score between 0-74.5
  b. Scaled Lung Score 2 (High Normal)=calculated lung score between 74.5-149
  c. Scaled Lung Score 3 (Low Mild acute)=calculated lung score between 150-165
  d. Scaled Lung Score 4 (High Mild acute)=calculated lung score between 165-180
  e. Scaled Lung Score 5 (Low Severe acute)=calculated lung score between 181-250.5
  f. Scaled Lung Score 6 (High Severe acute):=calculated lung score between 250.5-320
  g. Scaled Lung Score 7 (Low Chronic)=calculated lung score between 320-400
  h. Scaled Lung Score 8 (Median Chronic)=calculated lung score between 400-500
  i. Scaled Lung Score 9 (High Chronic)=calculated lung score between 500 and above Calculated lung scores that fall close to or above these threshold levels of the Scaled Lung Scores indicate presumptive diagnosis of the corresponding conditions. For example, a calculated lung score of 175 would indicate a diagnosis of a high mild acute respiratory condition (Scaled Lung Score 4) and approaching a severe acute condition (Scaled Lung Score 5). A calculated lung score of 425 would indicate a median chronic condition (Scaled Lung Score 8), and one that represents disease of longer duration accompanied by some irreversible lung consolidation. Although the calculated lung scores are provided in distinct ranges, it shall be understood that calculated lung scores that fall close to the end of one range and the beginning of the next range may be worthy of further analysis by the caregiver to ensure the assignment of the lung score is consistent with other symptoms exhibited by the animal. Thus, the general ranges are an excellent indicators of lung conditions, but some lung scores may be worthy of additional analysis.

Additional filtering techniques may be used to improve analysis of the recorded sounds. Three additional filters that can be used to eliminate interfering sounds include a heartbeat reduction filter, an adaptive bandstop filter, and a pop/crackle filter. The heartbeat filter is based on an adaptive threshold piece wise interpolation technique that is used to eliminate the noise associated with the heartbeat and that can otherwise interfere with recorded lung sounds. The adaptive bandstop filter is based on the same technique as the heartbeat filter, but is instead focused on eliminating any interference noise emitted at a constant frequency throughout the recorded sound, such as the noise generated by a cattle chute. The pop/crackle filter is used to eliminate any remaining pops or crackles associated with stethoscope movement that remain on the user selection screen.

In accordance with basic functioning of the software of the present invention, a user can select a particular file that corresponds to recorded sound data for a particular animal taken at a particular time. This file can include other identifying information such as the location where the sound was recorded, how it was recorded (e.g., chute side and type of stethoscope used). Once the user has selected the particular file, a spectrogram of the sound along with the score for that sound is shown on a user interface. The spectrogram may include the use of various colors that indicate the amplitudes of the frequencies recorded. Also in accordance with the present invention, the numerical values of the lung scores can each correspond to one or more diagnoses taken from a database of diagnoses, a database of recommended treatment(s) for each diagnosis, and prognoses for improvement based on the diagnoses and recommended treatment(s). Accordingly, the user interface may also display the diagnoses, recommended treatments, and prognoses. The recommended treatments and prognoses will be generated from the calculated lung scores and other factors such as age, weight, days on feed, projected market date, season, origin history, risk category, and rectal temperature.

Also, the spectrograms assist a caregiver in further analyzing the particular pathology associated with the animal since there may be other indications within the spectrogram that assist the caregiver in making a diagnosis. For example, comparing the amplitudes of the recorded sounds during inhalation and exhalation can also be an indicator as to a particular respiratory condition.

With respect to a preferred device for capturing auscultated sounds from the bovine species, a preferred device would include a stethoscope incorporated within a chest piece that communicates either wired or wirelessly with a portable LCD touch screen that displays the spectrogram/waveform of the recorded sound. The portable LCD touch screen could be, for example, a personal digital assistant (PDA) that contains the necessary software to generate a screen display with the spectrogram of the recorded sounds. As discussed below, it is contemplated within the present invention that the user has the option of filtering extraneous data from the recorded wave forms so that the wave forms reflect accurate data corresponding to the actual sound emitted from the animal.

Various other features and advantages of the present invention will become apparent from a review of the following detailed description, taken in conjunction with the drawings.

BRIEF DESCRIPTION OF THE DRAWINGS

FIG. 3 is an example spectrogram showing normal lung sounds for bovine specie;

FIG. 4 is another spectrogram illustrating bovine lung sounds, categorized as mild acute;

FIG. 5 is another spectrogram illustrating bovine lung sounds, categorized as severe acute;

FIG. 6 is another spectrogram illustrating bovine lung sounds, categorized as chronic.

DETAILED DESCRIPTION

Figure 1:
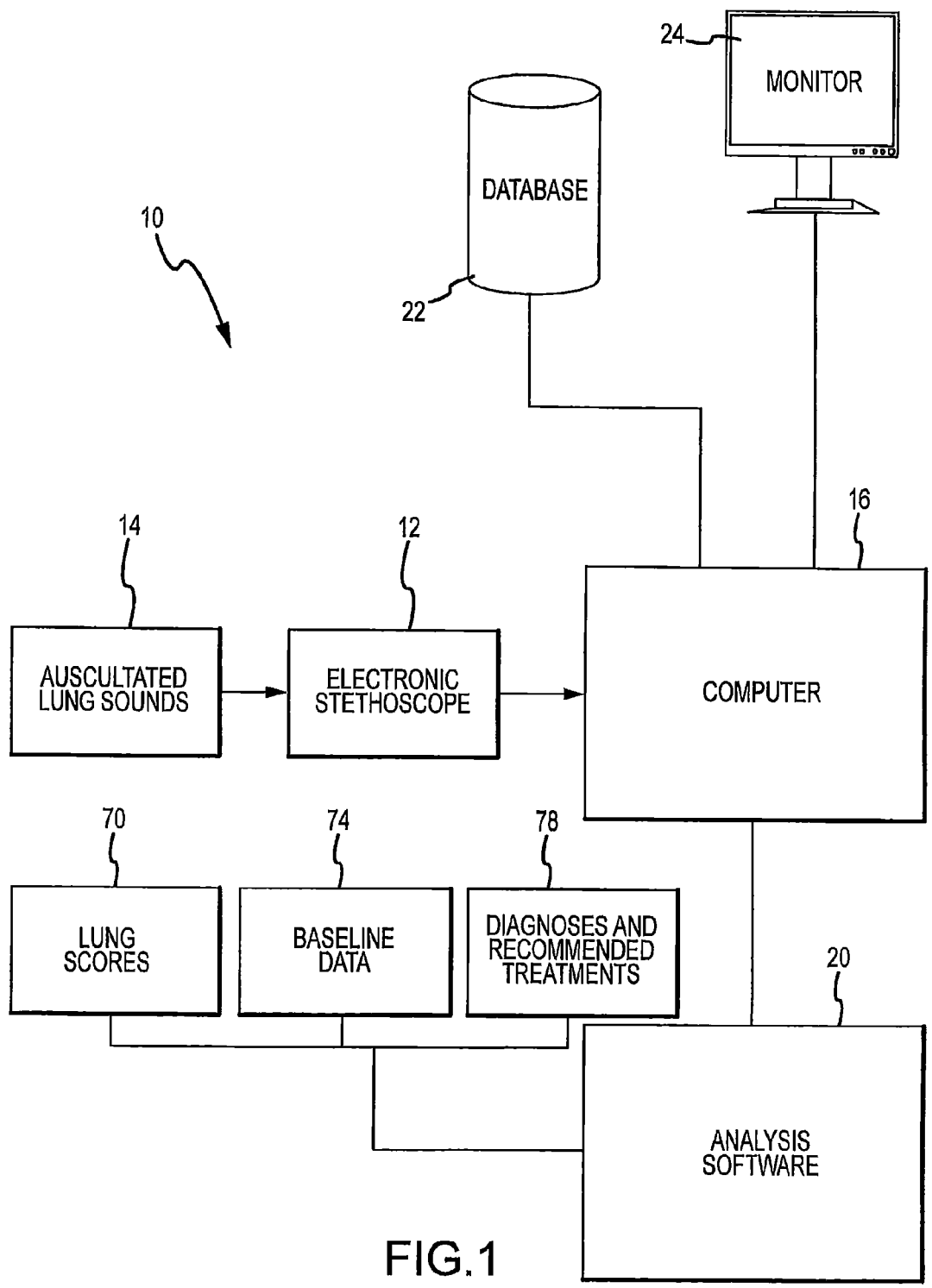
FIG. 1 is a schematic view of the system of the present invention.

Referring to FIG. 1, the system 10 of the present invention is illustrated. An electronic stethoscope 12 is used to gather lung sounds 14 from the animal. The stethoscope 12 detects the sounds, and the sounds are then downloaded in digital form to a computing device 16. The computing device 16 can take a number of forms, such as a standalone personal computer, a portable computing device such as a personal digital assistant (PDA) The computing device 16 includes a conventional microprocessor for manipulation of computer-coded instructions in the form of the analysis software 20. One or more databases 22 accessible by the computing device stores the digital sounds. A user interface such as a monitor 24 allows the user to view the gathered data, to include a spectrogram that may be generated by the analysis software 20 indicative of various attributes of the recorded sound to include frequencies, amplitudes, and other attributes that are recorded over time.

Figure 2:
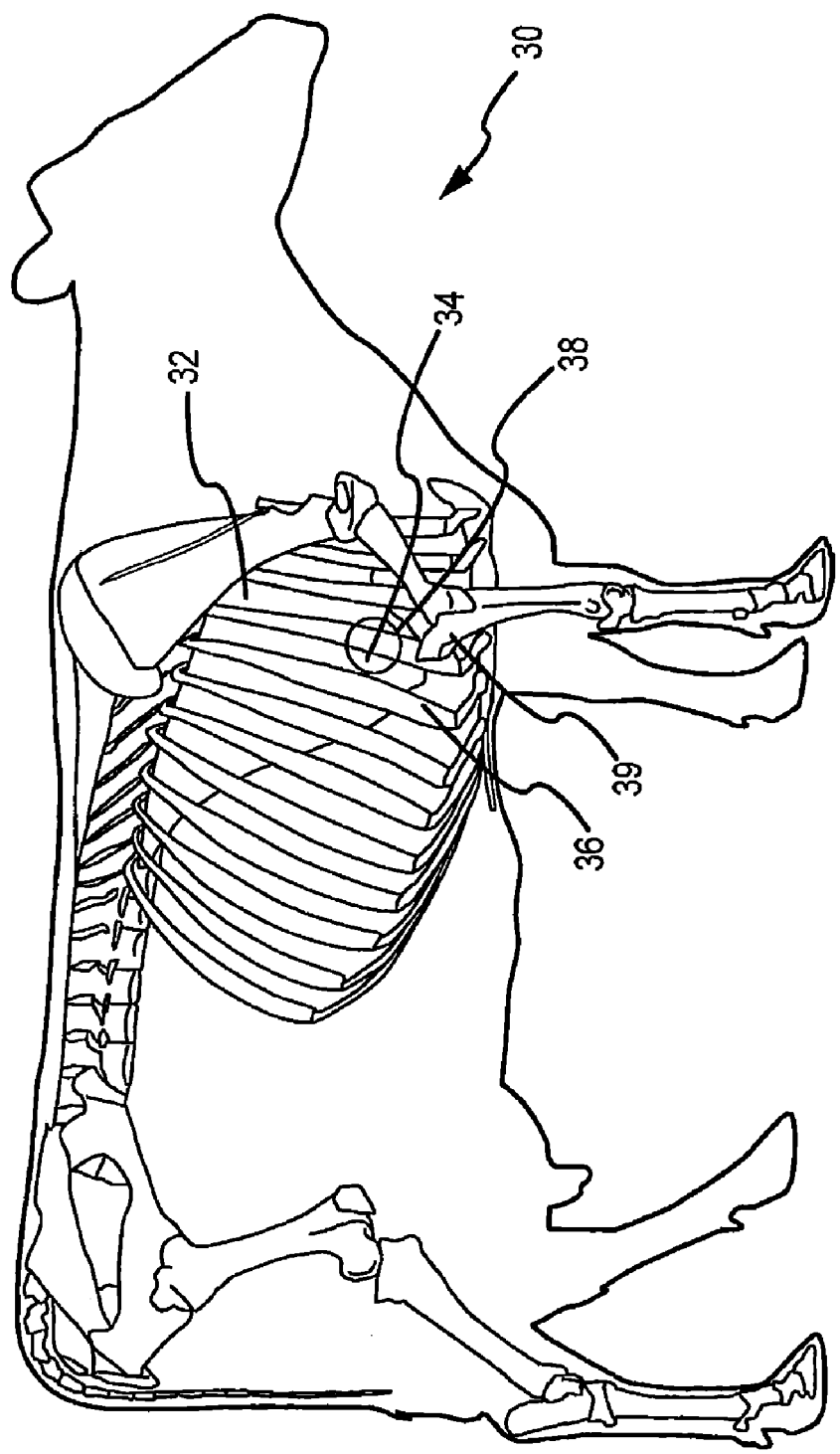
FIG. 2 is a schematic diagram of a bovine specie showing a preferred location where auscultated sounds are gathered, such as by an electronic stethoscope.

The auscultated lung sounds 14 are obtained from the animal in accordance with placement of the stethoscope at designated locations on the animal. Referring now to FIG. 2, a bovine 30 is illustrated with the lungs 32 located at a central region of the body. In this figure, the apical lobe 34 is the preferred location where the sensing device of the stethoscope is placed. As shown, the apical lobe 34 is covered partially by the fourth rib 36. The circle 38 illustrates the preferred location where the stethoscope should be placed, which is approximately three inches above the right elbow 39. With respect to placement of the digital stethoscope, the area 38 has been shown to be an optimum area for data gathering. The Bovine species possesses an extra lobe in their lungs compared to other animals such as humans, referred to as the right apical lobe ventilated by the most anterior accessory tracheal bronchi, making the apical lobe most susceptible to acute aerogenous pneumonia. If auscultated sounds are to be gathered from the left side of the animal, then the preferred location for placement of the stethoscope is approximately the same, i.e., three inches above the left elbow that results in placement of the stethoscope over the cardiac lobe. However on the left side, positioning the stethoscope between the fourth and fifth ribs may provide a better position for gathering the sound. Given that bovines stand on all fours, respiratory disease is typically aerogenous in origin and tends to concentrate first in the apical lobe, progresses to the left cardiac lobe, and then ventrally to the additional lung field. Once the stethoscope takes the recorded sound, this data is then transferred to the computer 16 in accordance with known data transfer techniques. Preferably, the recorded sound taken by the stethoscope is a .wav file. Once the data is loaded and stored in the database 22, the analysis software 20 performs certain manipulations of the data in order to generate a number corresponding to a calculated lung score 70 as discussed below.

In accordance with the present invention as mentioned in the Summary, an algorithm is applied to the data within the .wav file in the form of a short-time Fourier transform that is performed on the raw data with a window size of approximately 512 data points and an approximate overlap of 50%. A Hamming function can be used as the windowing function. As discussed below with respect to FIGS. 3-7, the resulting data from each transform is plotted to form data points for a spectrogram that may be viewed by the user.

From various investigations, it has been determined that amplitudes of frequencies between 500-900 Hz represent those data points that can be numerically manipulated within an algorithm to indicate various levels of disease within an animal. As mentioned above, the data can be split into ten basic sets or bands, namely, amplitudes from 500-540 Hz, 540-580 Hz, 580-620 Hz, 620-660 Hz, 660-700 Hz, 700-740 Hz, 740-780 Hz, 780-820 Hz, 820-860 Hz, and 860-900 Hz. Calculations are made to then determine the calculated lung scores 70. The resulting scores are compared to established baseline data 74 that indicate some level of disease within the animal. As also mentioned in the Summary, Scaled Lung Scores can be used that correspond to ranges of the calculated lung scores to assign diagnoses for the level of disease within the animal. Recommended treatments may then be established based on the diagnoses. The diagnoses and treatments may also be stored in the database 22 wherein the diagnoses may be listings of particular lung ailments, and the treatments may include descriptions of various medications to be administered to the sick animal.

A perfectly healthy animal will ideally have little or no sound generated within the targeted frequency range and, therefore, a calculated score of 0 or a value much less than 75 would be calculated. Variation of lung sounds in normal cattle does occur and these variations are subject to a number of factors to include biological variation, digestive function, and immune status. Accordingly, it is also contemplated that the specific lung scores assigned to the various diagnoses can be shifted to account for any systemic variations that may occur in a group of animals. For calculated lung scores of approximately 150, the diagnosis will be low mild acute (Scaled Lung Score 3), indicating the presence of edema and exudates accompanied by reduced airflow through still functional tissue. These changes are very dynamic and have the potential to quickly become more severe in the absence of therapy and conversely, the animal's condition could dramatically improve in the presence of appropriate therapy. For calculated lung scores that occur between 0 and 149, there is considerable discretion by the caregiver to determine whether the animal has respiratory disease of any concern. Other factors may be analyzed, to include whether the animal has other signs of disease such as a temperature, depression, nasal discharge, etc. For calculated lung scores that reach 181, again through testing, it has been shown that these animals certainly have a level of respiratory disease that should be treated. Accordingly, at 181, the severe acute diagnosis is made which further indicates severe inflammatory responses including edema, effusion, and early consolidation in airways and alveolar spaces that is drastically reducing the efficiency of respiration. These cases deserve aggressive therapy, supportive care, and are at greater risk to require further therapy. For calculated lung scores that may fall between 150 and 181, the caregiver has a certain amount of discretion in determining the actual disease in the animal, and further evaluation of the animal can take place to confirm the nature of the disease. For calculated scores that reach 320, a chronic diagnosis can be made and some amount of nonfunctional lung tissue is typically involved in irreversible consolidation, coagulative necrosis, and possible abscess formation. For calculated lung scores falling between 181 and 320, again the caregiver has certain discretion in determining the actual nature of the respiratory disease occurring within the animal. For calculated scores above 320, it has been shown through testing that these animals have suffered some degree of irreversible loss of respiratory function that will decrease performance potential. Therapies depend on the percentage of lung involved, and the therapies are aimed at salvaging normal tissue and reducing abscess formation. Optimum treatment response and prudent antibiotic use depends on matching lung pathology associated with particular lung scores with pharmokinetics of antibiotics and ancillary drugs generated by a dynamic data base.

Now referring to FIG. 3, an example spectrogram 40 is illustrated which corresponds to a spectrogram that may be viewed by the user on the monitor 24 as a result of the analysis software 20 generating the spectrogram based upon data gathered from various observations. In this Figure, the spectrogram 40 includes data plotted as a function of the frequency of the sounds 42 over a period of time 44. More specifically, the frequencies are plotted in increments of 250 Hz, and sound is plotted over seconds. As shown in this Figure, the data points 46 show that there is only one occurrence of a sound that is above 500 Hz, therefore indicating a generally healthy animal. In this example, after application of the mathematical operations/algorithms, the diagnosis would in fact be normal. At the 0.80-second data point there is a single spike 47 that is greater than 500 Hz; however, this particular data point may be attributed to noise, such as background noise or even perhaps the heartbeat of the animal. Since this one data point is not repetitive over time, this data point can be ignored. In any event, even when this single data point is included in the data manipulated by the mathematical operations/algorithms, the lung score would still be near zero, therefore indicating very little lung pathology. The trimming function described above can remove much of the irrelevant background or environmental noise, such as pops or clicks generated from the stethoscope. A heart beat filter can reduce any existing heart beat noise, and constant noise at a particular frequency can also be removed using the noise filter. As mentioned, it is preferable to apply selected filters to eliminate as much noise as possible, such as background noise created by a heartbeat. This spectrogram may also be illustrated in color where volumes of the plotted frequencies correspond to particular colors.

Referring to FIG. 4, another spectrogram 40 is illustrated in which the amplitudes of the frequencies include a few data points 48 that fall between 500 and 900 Hz. After application of the mathematical operations/algorithms, this spectrogram is exemplary of one that could indicate a mild acute diagnosis. Since a caregiver does not have to make a diagnosis by merely looking at the spectrogram, the degree of subjectivity in making the diagnosis is greatly reduced therefore resulting in much more accurate diagnoses based on recorded data.

Referring to FIG. 5, the recorded sound shown in the spectrogram 40 is an example of one resulting in a severe acute diagnosis after application of the mathematical operations/algorithms. As shown, a number of additional data points 50 in this spectrogram fall between 500 and 900 Hz as compared to the data points 48 in the spectrogram of FIG. 4.

Referring to FIG. 6, yet another spectrogram 40 is shown illustrating a situation in which a chronic diagnosis can be made as reflected in the marked increase in the amplitude of the upper frequencies. As shown, there are many data points 54 that occur above 500 Hz that for each breath of the animal. After application of the mathematical operations/algorithms, this spectrogram indeed would result in a lung score corresponding to the chronic diagnosis.

As mentioned, in order to provide the most reliable sets of data to include the capability of visually displaying data in the form of spectrograms, it may be necessary to apply certain filters to the gathered data to eliminate various sources of noise. As mentioned, filtering techniques may be used to improve analytical data. These filters may include a heartbeat reduction filter, a pop/crackle filter, and a noise filter. All three filters will be based on an adaptive threshold piecewise interpolation technique. The heart beat filter will be focused on detecting periodic high amplitudes in the 0-250 Hz frequency range. The pop/crackle filter will be focused on periodic extremely high amplitudes in the 500-2000 Hz range. The noise filter will be focused on continuous high amplitudes in the 500-1000 Hz range. Whenever a section is detected by any of the filters, it is removed. The missing data is filled in by a linear interpolation. Unlike the collection of human sounds that may require a large bank of microphones to collect sound, assuming the electronic stethoscope is properly placed; diagnosis and treatments with the present invention can be accurately predicted by use of a single stethoscope. The Fourier transform brings the collected data into the frequency domain, thereby allowing the analysis software to determine which frequencies are contained in the sound and at which volume those frequencies exist. In general, the louder the sound at the frequencies of interest (500-900 Hz), the higher the lung score for the animal.

While the data obtained in the present invention can be an accurate predictor of the health of bovine species, the technique described herein would provide no useful diagnosis for humans. Human respiratory disease is typically far less severe than that of bovines, and the particular volumes and frequencies in humans would be much smaller over a long period of time. Human respiratory diseases are often signified by specific types of wheezes and crackles that have very specific lengths, volumes and frequency levels, none of which correspond to a similar diagnosis for bovine species.

Figure 7:
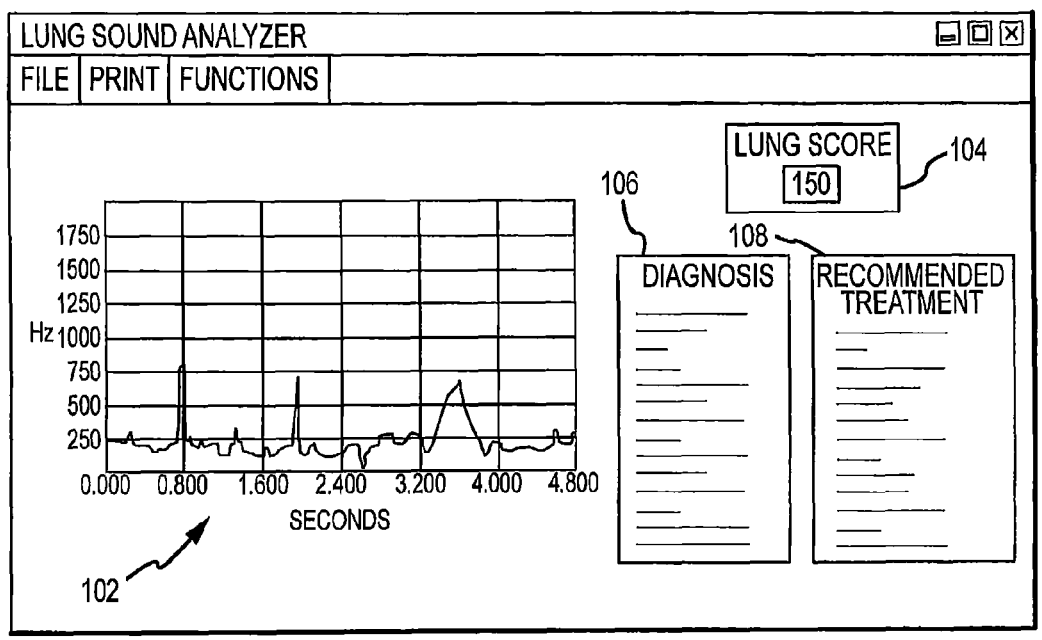
FIG. 7 is an example user interface screen showing a spectrogram, the calculated lung score corresponding to the spectrogram, a diagnosis, and one or more recommended treatments.

FIG. 7 is an example user interface screen 100 that includes a spectrogram 102, along with a corresponding display of the calculated lung score 104, a diagnoses 106, and a recommended treatment 108. In lieu of the calculated lung score, the Scaled Lung Score could be displayed on the screen. As mentioned above, the lung score may correlate to a diagnosis as well as one or more recommended treatments.

Figure 8:
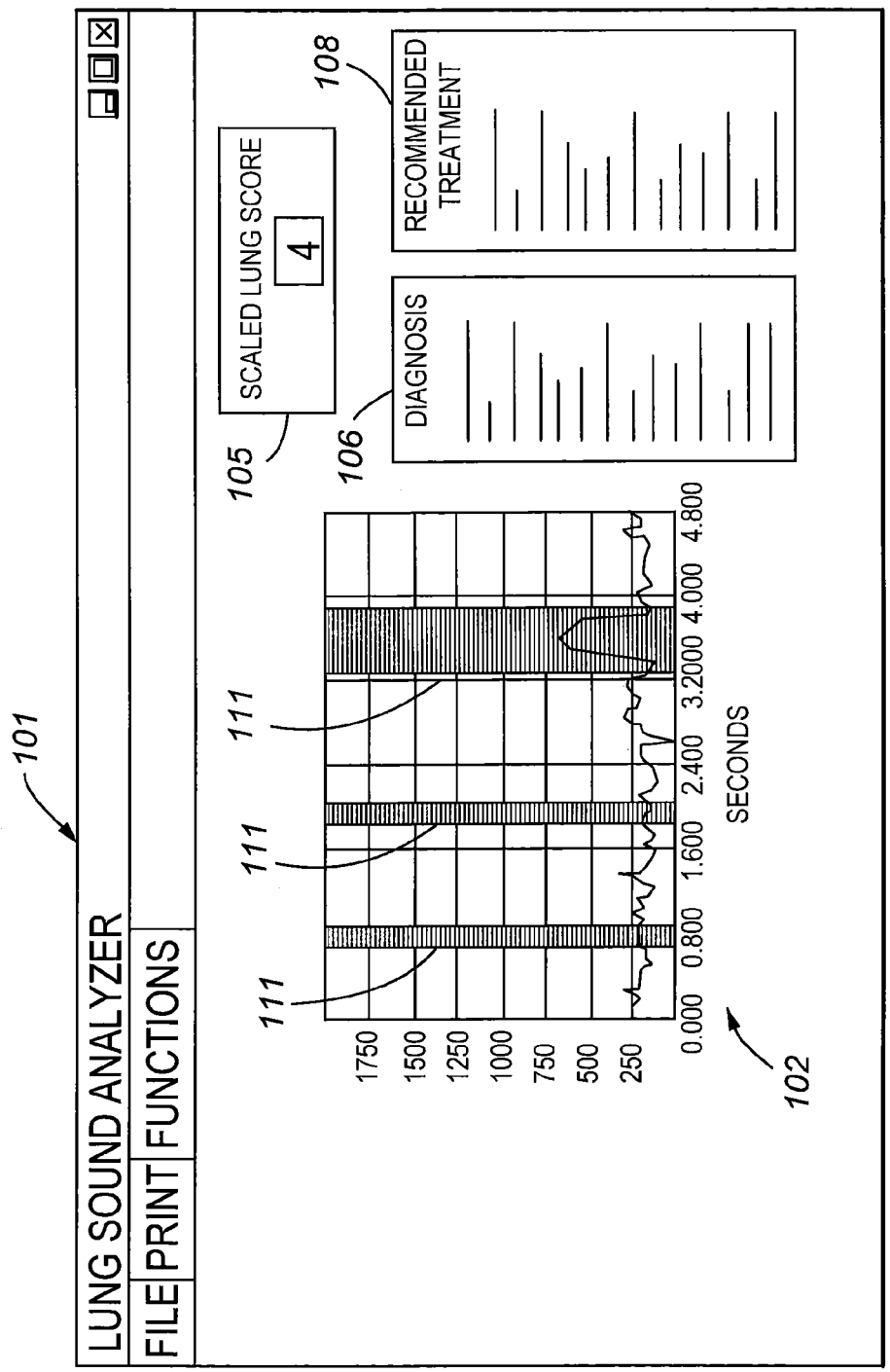
FIG. 8 is another example user interface screen showing the spectrogram of FIG. 7, wherein a user has trimmed frequencies that correspond to noise or other interfering frequencies not related to the targeted auscultated sounds of the animal.

FIG. 8 is another example user interface screen 101 that includes the spectrogram 102 of FIG. 7, a Scaled Lung Score 105, a diagnosis 106, and the recommended treatment 108. This screen 101 also shows those portions 111 of the spectrogram that the user has highlighted for removal as data that is not accurate in terms of the actual lung sounds. The portions 111 to be removed are noise or other interfering frequencies not related to the actual auscultated sounds of the animal. These interfering frequencies are identified as peaks in the spectrogram with amplitudes that are clearly out of range as compared to the remaining portions of the spectrogram. As mentioned, these interfering frequencies can be attributed to factors such as noise from the stethoscope, the heartbeat of the animal, etc. Once these areas have been trimmed, the user may again view the modified spectrogram to ensure the data appears accurate.

Other factors may also be considered when generating automatic diagnosis and treatments, such as other symptoms of the animal being analyzed. Therefore, it is also contemplated with the present invention that the automatic diagnoses and treatments can be further modified by analyzing other data such as the rectal temperature, projected market date, and risk category.

Figure 9A:
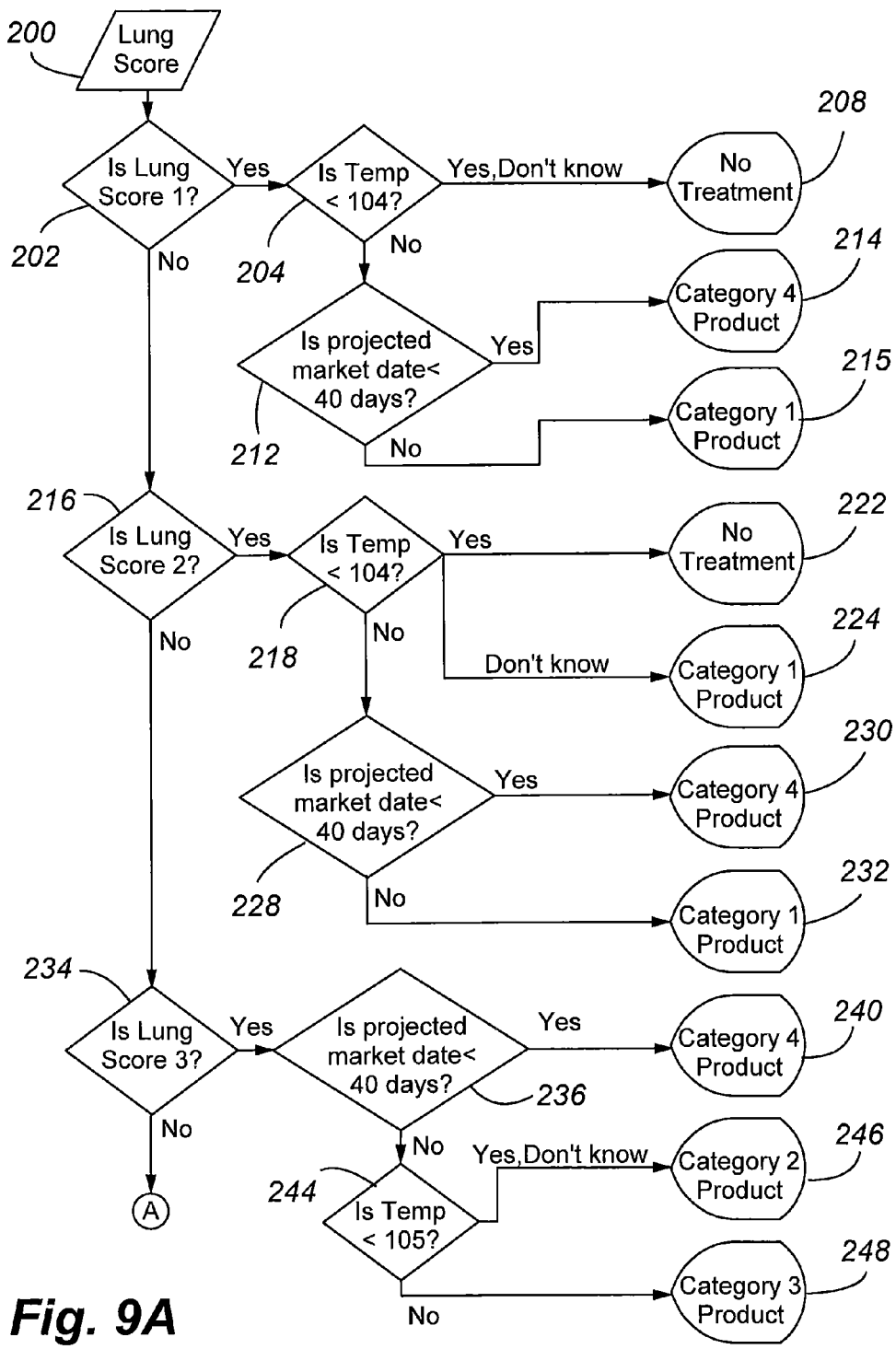
FIGS. 9A and 9B illustrate a flow diagram of a dynamic treatment matrix that provides a recommended treatment based upon consideration of a number of factors to include lung scores.
Figure 9B:
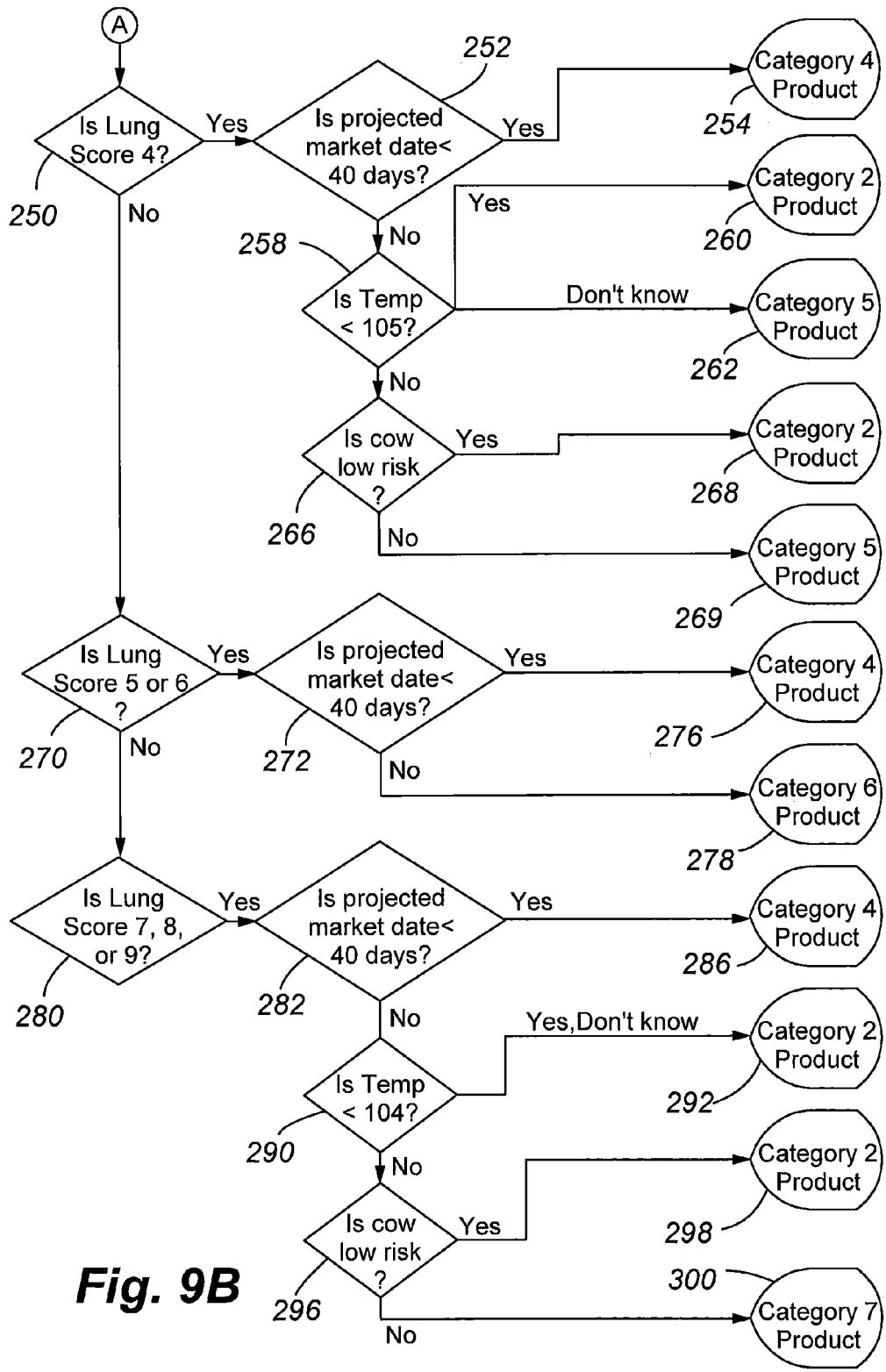

Referring to FIGS. 9A and 9B, a flowchart is provided for determining an appropriate treatment based upon a combination of these factors. The flowchart of FIGS. 9A and 9B may also be referred to as a dynamic treatment matrix that takes into consideration the various factors to determine an appropriate treatment. It shall be understood that in accordance with the method of the present invention, the only requirement for determining a recommended treatment is the determination of a lung score. The rest of the factors included within the dynamic treatment matrix are optional, but may provide a caregiver with additional treatment options if the other factors combine in a manner that may suggest an additional or perhaps a modified treatment.

In the recommended treatments within the matrix, the current pharmaceuticals are assigned a set of attributes that match designated lung scores. For example, one particular drug could work well on mild acute lung scores. Given that drugs change quite frequently, the current available drugs are stored in a database that is continually updated, ensuring that each drug is assigned the appropriate characteristics or case definition as set forth in the determination of the lung scores. Initially, the treatment recommended derives primarily from the lung score. In order to further consider the best match of the drug to be prescribed, the pharmaceuticals can also be assigned a set of attributes that match secondary considerations, such as whether the drug has shown good results for cattle having high rectal temperatures or good results for low risk cattle.

It is also contemplated with the present invention that historical data can be maintained for past treatment recommendations based upon the lung scores or other factors considered at the time. The historical analysis will include an evaluation of how successful treatment was, and the rate of treatment success can then be balanced against the treatment provided to alter or shift a recommended treatment.

The recommended treatments in FIGS. 9A and 9B are recommended administrations of various drug categories. The categories are defined as follows: Category 1 are low cost, broad spectrum antibiotics; Category 2 are low cost, broad spectrum antibiotics with a slightly broader spectrum capability; Category 3 are broad spectrum antibiotics aimed at log growth phase; Category 4 are broad spectrum antibiotics with withdrawal times less than forty days; Category 5 are broad spectrum antibiotics aimed at log growth phase with the addition of RNA synthesis inhibitors with an affinity for lung tissue; Category 6 are state-of-the-art, broadest spectrum antibiotics; and Category 7 are broadest spectrum antibiotics with highest affinity for consolidated lung tissue.

With respect to the risk levels recited as factors in FIGS. 9A and 9B, the following definitions apply: 1. High risk cattle are those that are any of the following: freshly weaned, co-mingled (purchased one or two at a time from many herds), auction market cattle (i.e. sold at a livestock yard), or an absence of vaccination history and 2. Low risk cattle are those cattle that do not meet any of the criteria for high risk.

Referring now to the flowchart beginning at FIG. 9A, at Block 200, the lung score is determined. At Block 202, if the Scaled Lung Score is 1, then at Block 204 the next determination is whether the temperature of the animal is below 104° F. The rectal temperature is used as the baseline temperature for this flowchart. If the temperature is less than 104° F., then at Block 208, the recommendation is no treatment. If the temperature is greater than 104° F., then at Block 212, the next determination is whether the projected market date is less than 40 days. If the projected market date is less than 40 days, then the treatment recommended at Block 214 is a Category 4 product. If the projected market date is not less than 40 days, then the recommended treatment at Block 215 is administration of the Category 1 product.

Referring to Block 216, if the Scaled Lung Score is 2, the next determination at Block 218 is whether the temperature is less than 104° F. If the temperature is less than 104° F., then the recommended treatment at Block 222 is no treatment. If the temperature is not known at Block 218, then the recommended treatment at Block 224 is administration of a Category 1 product. If the temperature is not less than 104° F., then the next determination is the projected market date at Block 228. If the projected market date is less than 40 days, then the recommended treatment is administration of a Category 4 product at Block 230. If the projected market date is not less than 40 days, then the recommended treatment is a Category 1 product at Block 232.

Referring to Block 234, if the Scaled Lung Score is 3, the next determination is whether the projected market date is less than 40 days at Block 236. If the projected market date is less than 40 days, then the recommended treatment is a Category 4 product at Block 240. If the projected market date is not less than 40 days, then the determination is made if the temperature is less than 105° F. at Block 244. If the temperature is less than 105° F., or if the temperature is not known, then the recommended treatment is administration of a Category 2 product at Block 246. If the temperature is not less than 105° F., then the recommended treatment at Block 248 is administration of a Category 3 product.

Referring to Block 250, if the Scaled Lung Score is 4, then the next determination is whether the projected market date is less than 40 days at Block 252. If the projected market date is less than 40 days, then the recommended treatment is administration of a Category 4 product at Block 254. If the projected market date is not less than 40 days, then at Block 258 a determination is made whether the temperature is less than 105° F. If the temperature is less than 105° F., then the recommended treatment is administration of a Category 2 product at Block 260. If the user does not know the rectal temperature, then the recommended treatment at Block 262 is administration of a Category 5 product at Block 262. If the temperature is not less than 105° F., then the next determination is made at Block 266 whether the animal is categorized as low risk. If the animal falls within the low risk category, then the recommended treatment is administration of a Category 2 product at Block 268. If the risk category is not low, then the recommended treatment is administration of a Category 5 product at Block 269.

Referring to Block 270, if the Scaled Lung Score is a 5 or 6, then the determination at Block 272 is whether the projected market date is less than 40 days. If the projected market date is less than 40 days, then the recommended treatment at Block 276 is administration of a Category 4 product. If the projected market date is not less than 40 days, then the recommended treatment at Block 278 is the administration of a Category 6 product.

Referring to Block 280, if the Scaled Lung Score is a 7, 8 or 9, then the determination at Block 282 is whether the projected market date is less than 40 days. If the projected market date is less than 40 days, then the recommended treatment is administration of a Category 4 product at Block 286. If the projected market date is not less than 40 days, then the next determination at Block 290 is whether the temperature is less than 104° F. If the temperature is less than 104° F. or if the temperature is unknown, then the recommended treatment is administration of a Category 2 product at Block 292. If the temperature is not less than 104° F., then the next determination is whether the animal is low risk at Block 296. If the risk factor is low, then the recommended treatment at Block 298 is administration of a Category 2 product. If the risk factor is not low, then the recommended treatment is administration of a Category 7 product at Block 300.

Although the present invention has been set forth with respect to one or more preferred embodiments, it shall be understood that various other changes and modifications can be made to the invention in accordance with the scope of the claims appended hereto.

What is claimed is:

1. A system for diagnosing bovine diseases using auscultation analysis, said system comprising:
   a processor for processing auscultated lung sounds obtained from a bovine in the form of digital sound data detected by a stethoscope;
   computer coded instructions for manipulating the digital data through incorporation of at least one algorithm used to calculate a numerical lung score, said algorithm utilizing values of selected frequencies of the auscultated sounds;
   a database for storing data reflective of diagnoses, treatments, and prognoses that correspond to a plurality of baseline numerical lung scores; and
   a user interface for displaying a spectrogram reflective of the auscultated lung sounds, and displaying the lung score as it is associated with at least one of a corresponding diagnosis, treatment, and prognosis.

2. A system, as claimed in claim 1, wherein:
   said stethoscope is an electronic stethoscope that detects auscultated sounds, and converts the auscultated sounds to a digital format for transfer to the processor as the digital sound data.

3. A system, as claimed in claim 1, wherein:
   the detected sound is loaded into the computer from the stethoscope as a .wav file.

4. A system, as claimed in claim 1, wherein:
   the digital sound data is stored in an array, and a short-time Fourier transform is performed on the digital sound data to place the sound data in a frequency domain.

5. A system, as claimed in claim 4, wherein:
   the data from said Fourier transform is separated into groups of amplitudes of frequencies as follows: 500-540 Hz, 540-580 Hz, 580-620 Hz, 620-660 Hz, 660-700 Hz, 700-740 Hz, 740-780 Hz, 780-820 Hz, 820-860 Hz, 860-900 Hz.

6. A system, as claimed in claim 5, wherein:
   an algorithm is applied to the data in said groups of amplitudes of frequencies to obtain a calculated lung score, said algorithm being expressed by the following:

$x_1$=result of 500-540 Hz FIR filter; $x_2$=result of 540-580 Hz FIR filter; $x_3$=result of 580-620 Hz FIR filter; $x_4$=result of 620-660 Hz FIR filter; $x_5$=result of 660-700 Hz FIR filter; $x_6$=result of 700-740 Hz FIR filter; $x_6$=result of 700-740 Hz FIR filter; $x_7$=result of 740-780 Hz FIR filter; $x_8$=result of 780-820 Hz FIR filter; $x_9$=result of 820-860 Hz FIR filter; $x_{10}$=result of 860-900 Hz FIR filter; score=$0.205x_1+0.075x_2+0.02x_3+0.2x_4+0.35x_5+0.02x_6+0.02x_7+0.09x_8+0.01x_9+0.01x_{10}$.

7. A system, as claimed in claim 1, wherein:
   said lung score is compared to baseline data in the form of threshold values that generally correspond to bovine respiratory conditions, and wherein a recommended treatment is generated.

8. A system, as claimed in claim 1, further including:
   means for removing selected frequencies from said spectrogram attributed to noise whereby the lung score is calculated taking into account the removed frequencies.

9. A system, as claimed in claim 1, wherein:
   wherein said lung score displayed is at least one of a calculated lung score or a scaled lung score.

10. A system, as claimed in claim 7, wherein:
    said threshold values correspond to said conditions as follows:
    a) condition is low normal when said calculated lung score is between about 0 and 74.5
    b) condition is high normal when said calculated lung score is between about 74.5 and 149
    c) condition is low mild acute when said calculated lung score is between about 150 and 165
    d) condition is high mild acute when said calculated lung score is between about 165 and 180
    e) condition is low severe acute when said calculated lung score is between about 181 and 250.5
    f) condition is high severe acute when said calculated lung score is between about 250.5 and 319
    g) condition is low chronic when said calculated lung score is between about 320 and 400
    h) condition is median chronic when said calculated lung score is between about 400 and 500; and
    i) condition is high chronic when said calculated lung score is greater than 500.

11. A method for diagnosing bovine diseases using auscultation analysis, said method comprising:
    recording auscultated sounds emitted from a bovine and converting the sounds to digital data;
    applying a short-time Fourier transform on the digital data to convert the digital data to data in a frequency domain;
    determining amplitudes of frequencies present in the converted data in a range between about 500 and 900 Hz;
    separating the converted data having the amplitudes within the 500 to 900 Hz range into pre-determined groups;
    applying an algorithm to the converted data in the pre-determined groups to generate a lung score;
    comparing the lung score to baseline data, said baseline data indicating a level of pathology within the bovine based on the magnitude of the lung score;
    making at least one of a diagnosis, prognosis, and treatment recommendation based upon said comparison; and
    displaying the lung score and at least one of the diagnosis, prognosis or recommended treatment on a user interface.

12. A method, as claimed in claim 11, wherein:
    the data from said Fourier transform is separated into groups of amplitudes of frequencies as follows: 500-540 Hz, 540-580 Hz, 580-620 Hz, 620-660 Hz, 660-700 Hz, 700-740 Hz, 740-780 Hz, 780-820 Hz, 820-860 Hz, 860-900 Hz.

13. A method, as claimed in claim 12, wherein:
    an algorithm is applied to the data in said groups of amplitudes of frequencies to obtain a calculated lung score, said algorithm being expressed by the following:

$x_1$=result of 500-540 Hz FIR filter; $x_2$=result of 540-580 Hz FIR filter; $x_3$=result of 580-620 Hz FIR filter; $x_4$=result of 620-660 Hz FIR filter; $x_5$=result of 660-700 Hz FIR filter; $x_6$=result of 700-740 Hz FIR filter; $x_6$=result of 700-740 Hz FIR filter; $x_7$=result of 740-780 Hz FIR filter; $x_8$=result of 780-820 Hz FIR filter; $x_9$=result of 820-860 Hz FIR filter; $x_{10}$=result of 860-900 Hz FIR filter; score=$0.205x_1+0.075x_2+0.02x_3+0.2x_4+0.35x_5+0.02x_6+0.02x_7+0.09x_8+0.01x_9+0.01x_{10}$.

14. A method, as claimed in claim 11, wherein:
said lung scores compared to baseline data in the form of threshold values that generally correspond to bovine respiratory conditions, wherein a recommended treatment is generated; and
said threshold values correspond to said conditions as follows:
   a) condition is low normal when said calculated lung score is between about 0 and 74.5
   b) condition is high normal when said calculated lung score is between about 74.5 and 149
   c) condition is low mild acute when said calculated lung score is between about 150 and 165
   d) condition is high mild acute when said calculated lung score is between about 165 and 180
   e) condition is low severe acute when said calculated lung score is between about 181 and 250.5
   f) condition is high severe acute when said calculated lung score is between about 250.5 and 319
   g) condition is low chronic when said calculated lung score is between about 320 and 400
   h) condition is median chronic when said calculated lung score is between about 400 and 500
   i) condition is high chronic when said calculated lung score is greater than 500.

15. A method for diagnosing bovine diseases using auscultation analysis, said method comprising:
recording auscultated sounds emitted from a bovine and converting the sounds to digital data;
converting the digital data to data in a frequency domain;
determining amplitudes of frequencies present in the converted data in a range between about 500-900 Hz;
separating the converted data having the amplitudes within the 500-900 Hz range into predetermined groups;
applying an algorithm to the converted data in the predetermined group to generate a lung score;
evaluating the temperature of the animal and a projected market date of the animal;
comparing the lung score to baseline data, said baseline data indicating a level of pathology within the bovine based on the magnitude of the lung score;
making at least one of a diagnosis, prognosis, and treatment recommendation based upon said comparison; and
displaying the lung score and at least one of the diagnosis, prognosis, or recommended treatment on a user interface.

16. A method, as claimed in claim 15, wherein:
said recommended treatment includes administration of a product in a preselected category.

17. A method, as claimed in claim 15, wherein:
converting the digital data to data in the frequency domain is conducted by applying a short-time Fourier transform on the digital data.

18. A method, as claimed in claim 15, wherein:
said lung score is compared to baseline data in the form of threshold values that generally correspond to bovine respiratory conditions, and wherein a recommended treatment is generated;
said threshold values corresponding to said conditions as follows:
   a) condition is low normal when said calculated lung score is between about 0 and 74.5
   b) condition is high normal when said calculated lung score is between about 74.5 and 149
   c) condition is low mild acute when said calculated lung score is between about 150 and 165
   d) condition is high mild acute when said calculated lung score is between about 165 and 180
   e) condition is low severe acute when said calculated lung score is between about 181 and 250.5
   f) condition is high severe acute when said calculated lung score is between about 250.5 and 319
   g) condition is low chronic when said calculated lung score is between about 320 and 400
   h) condition is median chronic when said calculated lung score is between about 400 and 500
   i) condition is high chronic when said calculated lung score is greater than 500.

19. A method, as claimed in claim 15, wherein:
said algorithm is expressed by the following:

$x_1$=result of 500-540 Hz FIR filter; $x_2$=result of 540-580 Hz FIR filter; $x_3$=result of 580-620 Hz FIR filter; $x_4$=result of 620-660 Hz FIR filter; $x_5$=result of 660-700 Hz FIR filter; $x_6$=result of 700-740 Hz FIR filter; $x_6$=result of 700-740 Hz FIR filter; $x_7$=result of 740-780 Hz FIR filter; $x_8$=result of 780-820 Hz FIR filter; $x_9$=result of 820-860 Hz FIR filter; $x_{10}$=result of 860-900 Hz FIR filter; score=$0.205x_1+0.075x_2+0.02x_3+0.2x_4+0.35x_50.02x_6+0.02x_7+0.09x_8+0.01x_9+0.01x_{10}$.

\* \* \* \* \*